United States Patent [19]

Sarstedt

[11] 4,216,782
[45] Aug. 12, 1980

[54] DEVICE FOR THE EXTRACTION OF BLOOD

[76] Inventor: Walter Sarstedt, 5223 Nümbrecht, Rommelsdorf, Fed. Rep. of Germany

[21] Appl. No.: 877,699

[22] Filed: Feb. 14, 1978

[30] Foreign Application Priority Data

Feb. 15, 1977 [DE] Fed. Rep. of Germany ....... 2706247
Feb. 15, 1977 [DE] Fed. Rep. of Germany ....... 2706303

[51] Int. Cl.² ............................................. A61B 5/14
[52] U.S. Cl. .............................. 128/764; 210/DIG. 23; 128/765
[58] Field of Search ......... 128/2 F, DIG. 5, 763–766; 210/83, DIG. 23, DIG. 24

[56] References Cited

U.S. PATENT DOCUMENTS

| 2,594,621 | 4/1952 | Derrick | 128/DIG. 5 X |
| 2,700,973 | 2/1955 | Ju | 128/DIG. 5 X |
| 3,901,219 | 8/1975 | Kay | 128/2 F |
| 3,965,889 | 6/1976 | Sachs | 128/2 F |
| 4,004,575 | 1/1977 | Sarstedt | 128/2 F |
| 4,020,831 | 5/1977 | Adler | 128/2 F |
| 4,073,288 | 2/1978 | Chapman | 128/2 F |

FOREIGN PATENT DOCUMENTS

| 2451171 | 5/1976 | Fed. Rep. of Germany .... 128/DIG. 5 |
| 2455631 | 5/1976 | Fed. Rep. of Germany .... 128/DIG. 5 |

Primary Examiner—Kyle L. Howell
Attorney, Agent, or Firm—Browdy and Neimark

[57] ABSTRACT

A device for the extraction of blood, comprising a cylindrical receiving container, a piston air-tightly guided and shiftable therein and a connecting socket for a cannula at one end of the container, wherein the cylindrical container has an opening in the wall at the end remote from the connecting socket for drawing the air out of this portion of the container, and a suction device for a slow and uniform drawing-off of air connected by a connecting hose with the said opening in the wall of the container. The piston is moved away from the connecting socket and in the direction of the opening when and as long as the suction device is drawing-off the air from the container.

16 Claims, 9 Drawing Figures

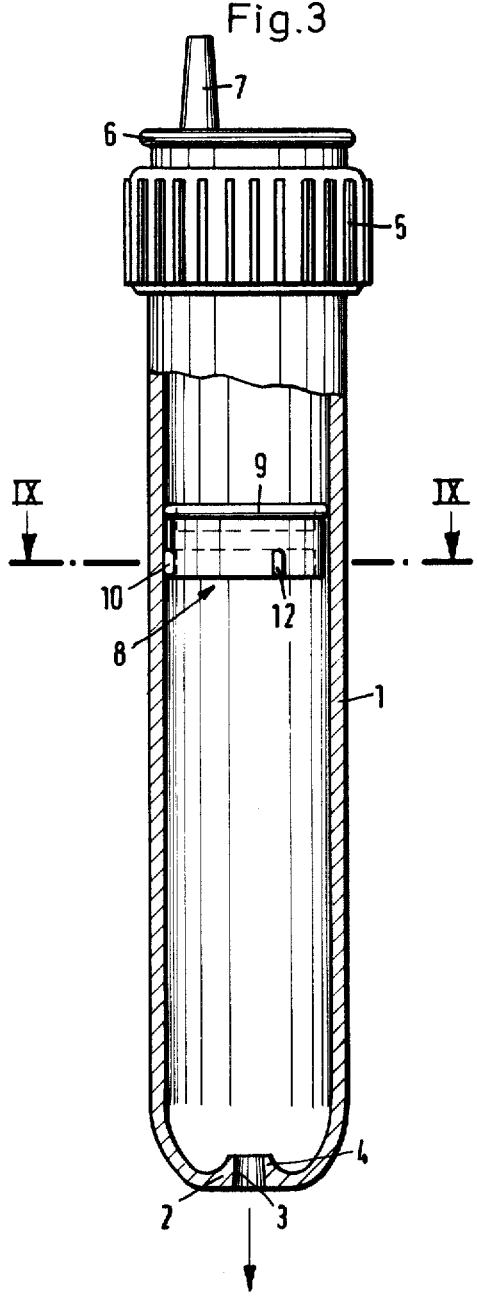
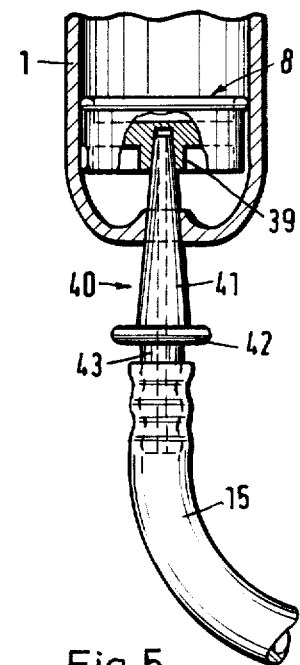
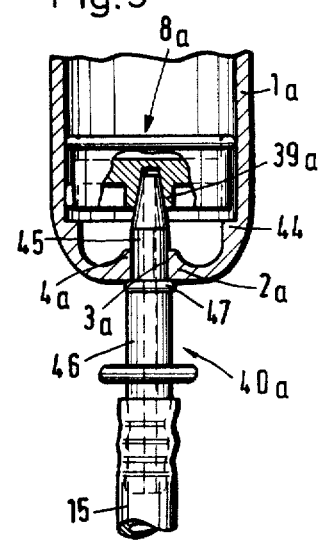

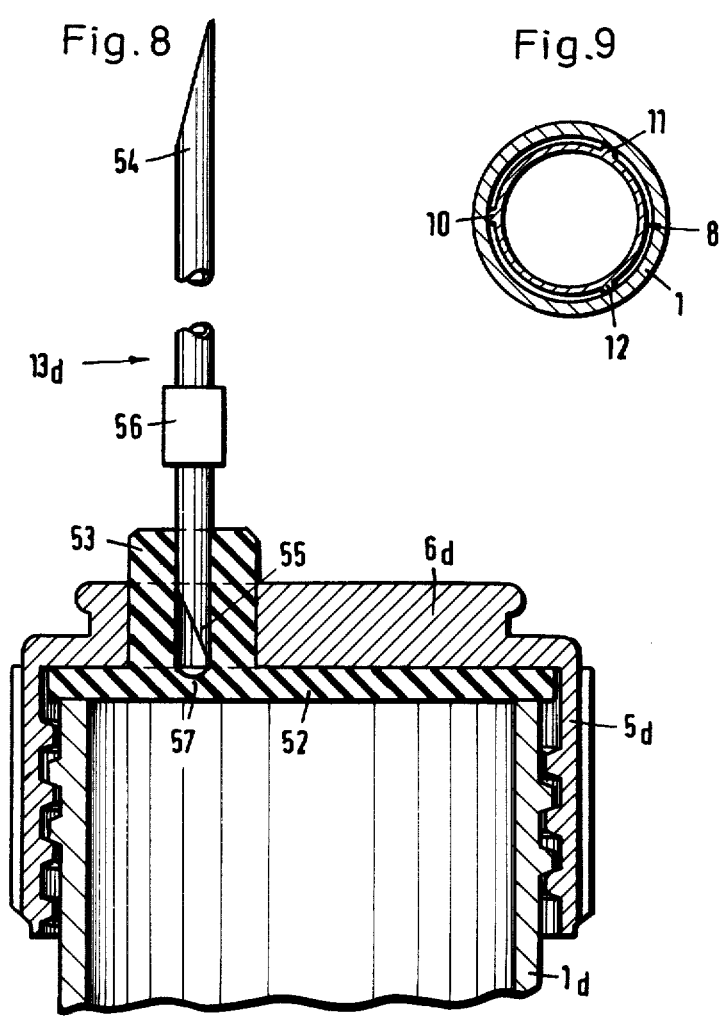

DEVICE FOR THE EXTRACTION OF BLOOD

This invention relates to a device for the extraction of blood, comprising a cylindrical receiving container, a hermetically guided and shiftable piston therein and a connecting socket at one end of the container for a cannula. Such receiving containers including a piston and a cannula are used for the extraction of blood, but also for injecting liquids as so-called syringes. For this purpose, the piston is provided with a piston rod and a grip and is initially brought into one of its limiting positions in the vicinity of the connecting socket for the cannula. Then, the cannula is introduced into the vein, and finally, the piston is slowly retracted. Thereby, the blood under pressure in the vein enters the cylinder through the cannula. When the piston is retracted so quickly that the blood is not able to enter through the cannula quickly enough, a subpressure occurs between the piston and the connecting socket which increases the flow velocity, but in doing so also gives rise to the risk of a damaging of the blood corpuscles.

The manipulation of these conventional blood extraction devices requires some skill and a calm hand so that it does not for instance occur that after insertion of the cannula point into the vein upon unskillfully retracting the piston the cannula point penetrates the opposite vein wall.

The invention intends to eliminate these difficulties and to permit a uniform and slow retraction of the piston. The device proposed according to the invention for the solution of this objective includes an opening in the wall of the cylindrical container at the end remote from the connecting socket for the cannula for withdrawing the air from this portion of the container, a suction device for a slow and uniform withdrawal of air and a connecting hose between the connecting socket of the suction device and the opening in the wall of the container.

By a withdrawal of the air from the container portion which is disposed between the opening and the piston there results a pressure differential at the piston which exerts a force thereupon and removes it from the connecting socket. The movement of the piston is terminated when it abuts the face of the cylindrical container at its end remote from the connecting socket.

Irrespective of the uniform and also, in case of a proper adjustment of the suction device, slow movement of the piston, the device according to the invention offers further advantages:

After insertion of the cannula into the vein, the doctor or some other operator needs only one hand for a calm holding of the cylindrical container, while the other hand is available for other operations to be done simultaneously or for holding the patient.

On the other hand, the connecting hose transmits no mechanical vibrations whatsoever which perhaps act upon the suction device to the cylindrical container with the cannula. This eliminates the risk of injuries of the opposite vein wall by an unskillful manipulation of the operator.

Principly, the piston in the cylindrical container may carry a piston rod which is guided through a central opening in a face closing the cylinder at its end opposite to the connecting socket for the cannula. In this case, the opening for the connection of the connecting hose conveniently is arranged adjacent to the central opening for the piston rod likewise in the face of the container. Preferably, however, it is proposed that the piston possesses no piston rod. In this case, the opening for the connection of the connecting hose may be arranged centrally in said face of the container.

Preferably, a connecting nipple is applied to the end of the connecting hose, said nipple being able to be inserted air-tight into the opening in the cylindrical container. The end of the nipple projecting into the cylinder then preferably possesses a tapered peripheral surface, and the piston possesses on its bottom side facing the face of the container centrally a tapered blind hole which corresponds to the taper of the nipple.

In this embodiment, after insertion of the nipple and withdrawal of the air the piston is retracted so far that it is positioned with said blind hole on the nipple and shuts it air-tight. In this position, the movement of the piston and thus the extraction of blood is terminated.

In order to draw the blood residue remaining in the cannula into the interior of the cylindrical container when withdrawing the cannula from the vein, the following arrangement is provided:

In the vicinity of the face an annular shoulder projecting from the inner wall of the cylindrical container is provided for supporting the piston. The dimensions and the association of the parts relative to one another are provided in such a way that upon abutment of the withdrawn piston with the nipple and upon sealing thereof by the tapered blind hole in the piston there is still a slight spacing between the bottom side of the piston and the said annular shoulder. When now the cannula point is withdrawn from the vein, with the same motion of the hand easily at the same time the nipple may be withdrawn from the cylindrical container. Thereby, as a result of the still maintained suction effect the piston is also moved until it abuts the annular shoulder. When the nipple is further withdrawn, it now is released from the blind hole, and the suction effect acting upon the piston is terminated. On the other hand, the cylindrical container is sealed by the piston abutting the shoulder. Thus, the cylindrical container may now directly be used as storage tube, and the blood may even be centrifugalized therein. It thus is not necessary to fill the extracted blood into a special centrifugalizing tube.

In order to further improve the sealing of the nipple by the retracted piston, it is preferred that from the face of the piston facing the inserted nipple a concentrically arranged boss with a tapered peripheral exterior projects, the tapered blind hole at the free end of the boss extending thereinto. Furthermore, in this embodiment, a collar with a tapered internal surface projects upwardly from the face of the container. The external taper of the boss of the piston then shortly before an abutment of the piston with the shoulder sealingly engages in the tapered bore of the collar.

The device according to the invention is furthermore improved in that the bore of the connecting socket for the cannula opening into the face of the container is sealed by a tearable film. Thereby, the interior later receiving the blood sample is kept free of contaminations, and also certain substances such as for preventing a blood coagulation may be introduced into this interior the premature escaping of which substances is prevented during transit by the film.

In furtherance of this concept it is provided for that the connecting socket for the cannula is a plug inserted into a bore of the face and consisting of a soft resilient material, which plug is intended to receive a cannula and is sealed in relationship to the interior of the cylindrical container by a weakened portion and by a predetermined tear portion, resp. In this case, a tube pointed at both ends and provided with a manipulation member is used as cannula.

In this instance, the advantage of the already mentioned tearable film in conjunction with a cannula pointed at both ends which is already known in a different context is used to effect the blood extraction in different ways, as desired:

Either shortly prior to inserting the outer point of the cannula the whole cannula is retracted in direction of the cylindrical container, the pointed rear end of the cannula tearing the weakened portion. Then the outer point of the cannula is introduced into the vein, and finally, the piston is retracted by the suction device.

On the other hand, the device may also be used as known from other blood extraction devices:

The cannula is first introduced into the vein with its outer pointed end, without the rear pointed end having already destructed the film. Then, the piston is moved by means of the suction device partially or even completely into its rearward limiting position so that there is a subpressure in the space above the piston. Finally, the cannula is then moved with its rear pointed end slightly against the weakened portion or conversely the cannula is held fast and the cylindrical container is moved slightly in direction of the cannula. As soon as the rear pointed end of the cannula has punctured the weakened portion, the blood flows into the evacuated space of the cylinder. This latter fashion of blood extraction in which a cannula pointed at both ends is used and in which after inserting the front point of the cannula into the vein the rear point punctures a weakened portion and the cannula is thereby brought into communication with a container evacuated before already per se is already known, but in this case the containers must be evacuated during production. The containers are to then maintain their vacuum during transit and up to their use by the doctor or in the hospital. Containers of plastic cannot cope with these requirements, however. Containers of glass or containers having an inner glass lining are sensitive to shock, however, and they are generally destroyed when they drop.

On the other hand, a sealing at the location where the pointed cannula is inserted into the plug of soft resilient material bears problems. It occasionally occurs with the conventional devices, therefore, that the doctor takes such a container which to his opinion is evacuated, introduces the cannula into the vein and then notes that the container has no vacuum any more. The doctor is then compelled to remove the cannula from the vein, to take a new container and to puncture the vein again.

These difficulties do not occur with the device according to the invention. The cylindrical container may be made of plastic just like the piston can, readily, and it is therefore virtually unbreakable. Also, the container is not supplied evacuated and stored evacuated, like the conventional container is, but the vacuum is produced only shortly prior to the intended blood extraction by retracting the piston. Leakages do not have any significance with the device according to the invention.

Basically, any suction device is suited as suction device for a movement of the piston in the cylindrical container. For instance, a small suction pump driven by an electric motor may be used. Then, however, a connection to an electric power system is required. If instead dry batteries are to be used for the operation of the electric motor, they must be exchanged from time to time. A blood extraction device is to be ready for use always, however, and it should be independent of an electric power supply, also, if possible.

For practical reasons, furthermore a manually operated piston pump must be ruled out, since for the operation thereof at least one hand, if not both hands of a person are required.

On the other hand, a larger buffer container may be used as suction device, which must then be evacuated by some pumps from time to time again, however.

Preferably therefore a particularly convenient suction device is proposed which is simple and reliable and requires no electric current for its operation. Such a suction device includes a cylinder closed at both ends, a piston with a piston rod shiftable therein and guided air-tight, said piston rod extending through a face of the cylinder sealed air-tight relative thereto and carrying at its free end a hand knob, furthermore an outlet provided with a check valve and an inlet likewise provided with a check valve at the end of the cylinder remote from the piston rod, as well as finally a connecting nipple communicating with the inlet and provided for the connecting hose to the cylindrical container. The suction device is arranged in such a way that the piston is positioned in the one limit position, namely at the end of the cylinder remote from the outlet and the inlet, the piston rod extending out of the cylinder for almost its entire length. When now by pressure on the hand knob the piston rod is depressed and thus the piston is moved to the other end of the cylinder, a subpressure results in the annular space between the piston rod and the cylinder, which subpressure tends to retract the piston into its starting position. Thus subpressure represents an ideal resilient means which after releasing the hand knob insures a uniform return movement of the piston.

When depressing the piston rod, the air which is contained in the cylinder between the piston and the outlet is urged through said outlet by the piston. An excpaing of this air through the inlet is prevented by the blocking check valve. As soon as the hand knob is released again, the subpressure in the annular space between the piston rod and the cylinder gradually retracts the piston again. Thereby, the space below the piston is increased again, and there a subpressure results which is compensated in that air is drawn from the connected connecting hose though the inlet the check value of which opens in this direction of flow. During this stroke, the check valve of the outlet is shut.

The course of the force acting upon the piston in dependence of its position may readily be varied and thus correlated to practical requirements in that in the starting position of the piston, i.e. with the piston rod extended, a certain air space is already provided betwen the piston and piston rod as well as the cylinder. The larger this initial air space, the softer the so-called resiliency of the suction device.

It is furthermore preferably provided for that a releasing lock hook is arranged at the cylinder, said hook engaging behind a detent projection at the hand knob and thus holding the device biased by a depression of the piston rod in this position initially. The lock hook may readily be released by depression of a releasing button in counteraction to the force of a spring.

While the mentioned suction device in this form may be realized as a small light-weight hand-held device so that it is particularly well suited for individual blood extractions, this suction device may be furthered in that it is also suited for the pneumatic operation of a large number of blood extraction devices consecutively. In this aspect, it is proposed to accommodate two or more cylinders of the mentioned type in a common block and to associate to each cylinder a piston with a sealingly projecting piston rod and a hand knob. Each cylinder then possesses an outlet and an inlet with accordingly counteracting check valves. All inlets are conveniently interconnected by a manifold which leads to a connecting nipple for the connecting hose. This connecting hose may then consecutively be re-attached from one container to the next. In this case several or all cylinders of the block may then be biased in advance, and the piston rod and the piston of a specific cylinder of the suction device may then be released respectively after connection of a container by releasing the respective releasing button.

For raising the safety level, a further check valve is provided intermediate the manifold and the connecting nipple for the connecting hose, said check valve reliably precluding an unintended escaping of air from the suction device even in the event an individual valve of a cylinder should fail.

The invention is explained in closer detail hereinafter on the basis of the drawings in embodiments by way of example. In the drawings:

FIG. 3 is a partially broken-away side elevational view of the cylindrical container of FIG. 1 to an enlarged scale;

FIG. 4 is a partial illustration of the container with an inserted nipple and a connecting hose;

FIG. 5 is a partial illustration of a further modified embodiment of the container;

FIG. 8 is an enlarged partial-sectional view similar to FIG. 7 of a modified embodiment; and FIG. 9 is a sectional view along line IX—IX of FIG. 3.

Figure 1:
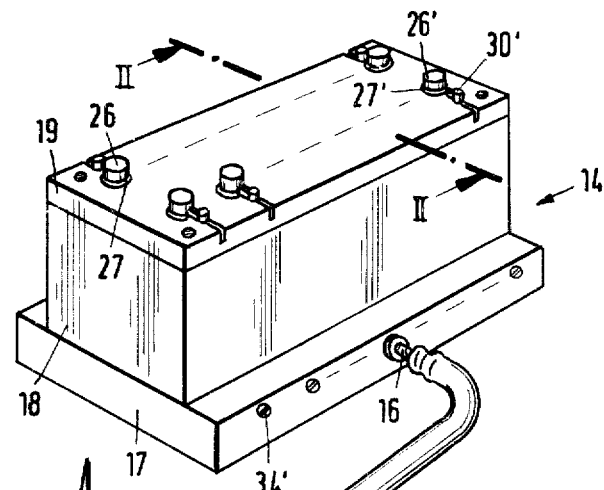
FIG. 1 is a simplified perspective illustration of a device according to the invention for the extraction of blood, comprising a suction device with a plurality of cylinders, a connecting hose and a cylindrical container with a cannula connected thereto.

The suction device 14 illustrated in FIG. 1 includes a base plate 17, a block 18 applied thereto, and a cover plate 19 as well as the further components built into these three parts and to be described hereinafter. A cylindrical container 1 for receiving the extracted blood is connected to a connecting nipple 16 of the suction device via a connecting hose 15 with a connecting nipple 40, said container having at its lower end a face with an opening for receiving the connecting nipple 40 and being closed at its upper end by a cap 5. This cap carries a connecting socket for a cannula 13. Details of this cylindrical container 1 will be described at length hereinafter.

The block 18 of the suction device possesses two rows of throughgoing bores 20 and 20' into which inwardly ground and possibly polished cylinders 21 and 21' are inserted. The cylinders are sealed at the bottom sides relative to the base plate 17 by annular seals 22 and 22' and at the top sides relative to the cover plate 19 by seal discs 23 and 23' which have a bore in their centers and are provided with a seal lip surrounding same for sealing the piston rod 25 and 25', resp.

In the cylinders, pistons 24 and 24' resp. are inserted having seals, and they are shiftable air-tight in the cylinders. The pistons are connected to the piston rods 25, 25' which carry hand knobs 26, 26' at their upper ends projecting from the cover plate 19. Said hand knobs serve the purpose of depressing the piston rods and thus the pistons.

Figure 2:
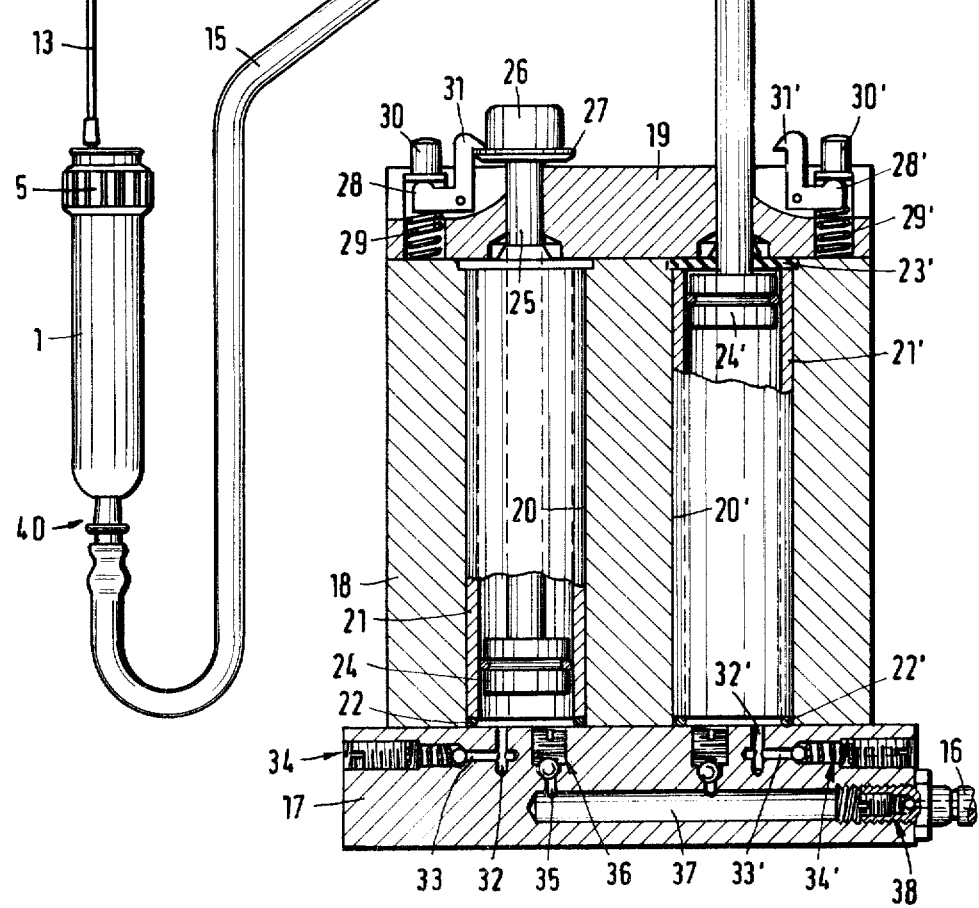
FIG. 2 is an enlarged sectional view along line II—II of FIG. 1.

The hand knobs 26, 26' carry projecting beads 27, 27' at their peripheries at the lower margins, said beads serving as detent projections for the tips of angular lock hooks 28, 31 or 28', 31'. These lock hooks are accommodated in slots of the cover plate and are pivotally mounted by pins. The cantilevers 28, 28' of these angular levers are urged upwardly by coiled compression springs 29, 29' so that the tips of the cantilevers 31, 31' engage behind the detent projections 27, 27' of the hand knobs 26, 26' and hold them, provided the piston rods are depressed, in their lower limiting positions. The lock hooks may be pivoted outwardly by operating buttons 30, 30' in counteraction to the force of the said springs, and thus the hand knobs may be released. In FIG. 2 the piston 24 has been illustrated in its lower limiting position, the right-hand piston 24' on the other hand in its upper limiting position.

Underneath the respective cylinder, there are openings in the base plate 17, said openings serving on the one hand for the escaping of air displaced by the piston during its downward stroke by accordingly oriented check valves 34, 34' and on the other hand leading to a manifold 37 via oppositely oriented check valves 36, 36' and conduits 35, 35'. This manifold is connected via a further check valve 38 to the connecting nipple 16 for the connecting hose.

As soon as the piston which has arrived in its lower limiting position and has been arrested by an engagement of the lock hook in this position is released by releasing the lock, the subpressure existing thereabove slowly drives it upwardly. In doing so, the cylinder space below the piston is gradually increased, and air is drawn from the connecting hose via the nipple 16, the check valve 38, the manifold 37 and the conduit 35 as well as the inlet valve 36.

When depressing the piston 24' illustrated at the right-hand side of FIG. 2 in its upper limiting position, the air underneath it is urged into atmosphere via the conduit 32', the conduit 33' and the outlet valve 34'.

The above described suction device which in the illustrated embodiment has sixteen cylinders with pistons suffices for practically all requirements of mass operation, for instance in hospitals. Work is started by depressing all hand knobs and by then releasing any piston by depressing an associated operating button. This piston then moves upwardly and draws in a certain amount of air which suffices for moving the piston in a cylindrical container 1 for small amounts of blood.

Upon connecting the next container, then simply some other piston 26 or 26' is released by depressing the associated operating button 30 or 30'. Thereby, sixteen blood extractions may be made consecutively without having to reload the suction device. It will also readily be noted which pistons are still in their lower limiting positions and consequently are available for the next blood extraction.

On the other hand, it also does not make any difficulties to bias or to load the relieved cylinders again by depressing the extended piston rods during the extraction of blood from a patient or also in between two blood extractions, without the operation of the blood extraction device being in any way impaired.

Finally, with the suction device described hereinbefore, also blood extraction devices for larger amounts of blood may be operated by then simply releasing simultaneously or even better consecutively two or more piston rods or pistons.

The cylindrical container 1 illustrated in FIG. 3 is provided at the bottom with a face 2 having a rounded transition and a tapered central opening 3 which is surrounded by a reinforcing bead 4. At the upper end, the container 1 is closed by a screwed-on cap 5 the face 6 of which possesses an eccentric bore which merges into an outwardly tapered connecting socket 7 for applying a cannula.

In the container 1, a piston 8 having no piston rod is guided shiftable and air-tight relative thereto. Sealing is effected by a seal bead 9, while a guiding to prevent tilting is effected by individual ribs 10, 11 and 12 extending parallel to the centerline. The arrangement of the ribs is clearly illustrated in particular in FIG. 9.

When drawing air from the opening 3 in direction of the arrow, a subpressure is produced between the face 2 and the piston 8, and the pressure differential at both sides of the piston urges it to move in direction of the face 2. In doing so, the space above the piston increases, between itself and the face 6 of the cap, and the subpressure thereby resulting causes the blood flowing from the vein into the cannula (not illustrated in FIG. 3) to flow into the interior of the container 1 above the piston 8 through the socket 7.

In FIG. 4, it has been illustrated in a preferred embodiment in a broken-away view that the piston 8 at the bottom and in its center has an annular boss 39 which upon a return movement of the piston finally, as illustrated in FIG. 4, sealingly abuts the tapered point 41 of a connecting nipple 40 inserted into the opening 3. The connecting nipple 40 possesses a retainer ring 42 and a corrugated boss 43 at the other side of this retainer ring, onto which boss the connecting hose 15 is pushed which is connectible at its other end to the initially described suction device.

In the modified embodiment according to FIG. 5, the connecting nipple 40a is first of all provided with a cylindrical portion 46 which at the top is closed by an abutment ring 47 which abuts the face 2a upon insertion of the point of the nipple 40a. Above the abutment ring 47, the nipple is likewise cylindrical, but has a smaller diameter. This portion 45 sealingly fits into the likewise cylindrical opening 3a in the face 2a of the cylindrical container 1a. This portion 45 is then taperedly convergent toward the free end and sealingly fits into a correspondingly tapered blind hole in the boss 39a of the piston.

Also, in this embodiment, there is a shoulder 44 projecting inwardly from the wall of the container 1a above the face 2a, namely at such a level that the bottom edge of the piston is still slightly spaced from the shoulder 44 when the boss thereof sealingly has engaged the tapered point of the nipple 40a. This embodiment brings about the following advantage:

When the stroke of the drawn piston is terminated in that the boss thereof sealingly engages the tapered point of the nipple 40a, the container is withdrawn, and thus the point of the cannula is removed from the vein. Then the total cannula is filled with blood which is desired to likewise be available for testing purposes. The blood is yielded from the cannula in that the nipple 40a is withdrawn by means of the retainer ring. The piston which is sucked tight with its boss on the tapered point of the nipple is in doing so guided downwardly together therewith to such an extent that it abuts the shoulder 44. This short stroke is rated such that it suffices in order to draw the blood remaining in the cannula into the container.

Figure 6:
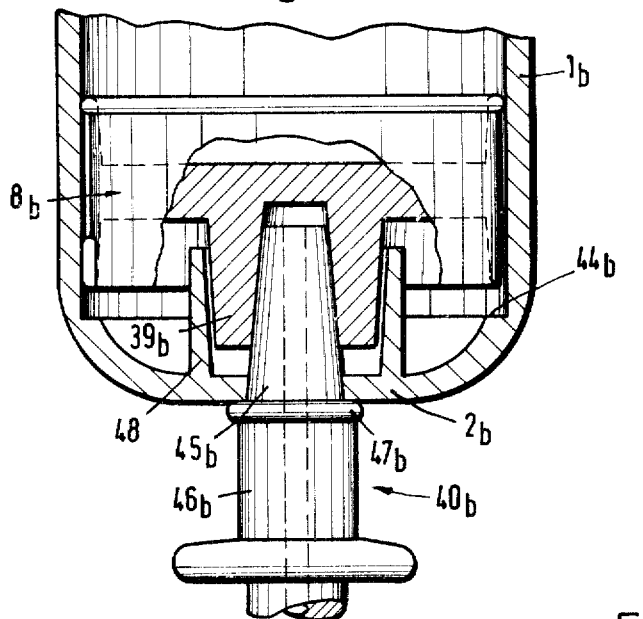
FIG. 6 is a partial illustration of a further modified embodiment of the container, to a larger scale.

In the modified embodiment illustrated in FIG. 6, the nipple 40b is likewise cylindrical in the portion 46b disposed underneath the abutment ring 47b, but is formed as a taper 45b thereabove, which, like in the embodiments of FIGS. 4 and 5, engages in the tapered blind hole in the boss 39b of the piston 8b and is thereby sealed.

In the embodiment of FIG. 6, a shoulder 44b also projects inwardly from the wall of the container 1b, said shoulder determining the end position of the piston 8b after withdrawing the connecting nipple 40b.

Contrary to the embodiments of FIGS. 4 and 5, in this instance a collar 48 having a tapered bore is provided which projects coaxially relative to the container 1b from the face 2b thereof and receives the boss 39b defining a corresponding outer taper in the end position and thereby insures an additional firm seating in this end position.

Figure 7:
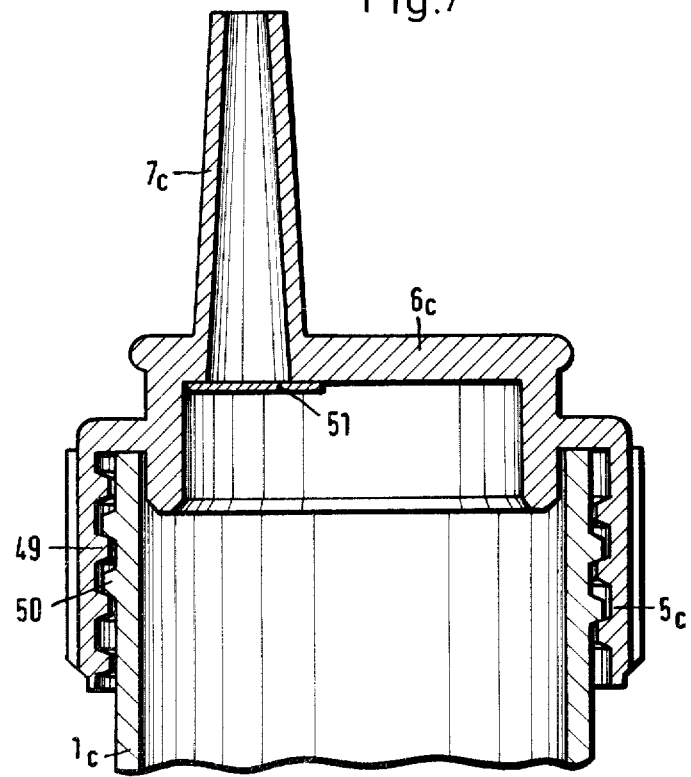
FIG. 7 is a partial illustration to the same scale as in FIG. 6 of the front end of the container.

FIG. 7 shows the upper end of the container, in particular its closure cap 5c which is screwed onto the upper end of the container provided with male threads 50 by means of its female threads 49. There is an opening in the face 6c of the closure cap 5c which opening is arranged eccentrically and merges with the inwardly and outwardly tapered connecting socket 7c onto which a cannula may be applied. The opening is closed by a tearable film 51 on the purpose of which explanations have already been given.

In the embodiment illustrated in FIG. 8, at the upper end of the container again a screwed-on cap 5d is provided with a face 6d and an eccentric opening. This opening in this instance is substantially wider and receives the cylindrical plug 53 of a soft resilient material which in turn has a bore for receiving a cannula 13. The plug 53 is integrally joined to a disc 52 which sealingly is trapped between the upper edge of the container 1d and the face 6d of the closure cap 5d when the cap 5d is screwed tight, with its periphery. The bore in the plug 53 for receiving the cannula 13d is formed as a blind hole and is confined at the bottom by a weakened portion 55 in the disc 52.

Next to the pointed front portion 54, the cannula 13d possesses a likewise pointed rearward portion 55 and a retainer ring 56 therebetween. The point of the portion 54 is introduced into the vein, while the point of the portion 55 finally by a backward movement of the retainer ring 56 punctures the weakened portion 57 and thus provides for a communication between the vein via the cannula and the interior of the container 1d.

After extraction of blood, the cannula is initially withdrawn from the vein. Subsequently, the cannula is drawn out of the disc 52 and the plug 53, the disc 52 thereby resiliently closing at the weakened portion 57 and thus preventing a flowing out of the blood from the container.

I claim:
1. A device for the extraction of blood, comprising:
   a cylindrical receiving container, closed at one end except for an opening in said one end;

a connecting socket connected to said container at the end opposite said one end and closing said end except for a socket connectable to a cannula which socket is open or openable into said cylinder;

a piston air-tightly guided and shiftable within said cylinder;

a connecting hose, one end of which is inserted in said opening in said cylinder; and suction means connected to the other end of said hose for applying a slow and uniform drawing-off of air, through said hose, from the portion of said cylinder between said piston and said one end having said opening.

2. A device in accordance with claim 1 wherein said suction means comprises:

a cylinder closed at both ends;

a suction means piston shiftably and air-tightly guidable within said cylinder;

a piston rod connected to said suction means piston and extending in an air-tightly sealed manner through one end of said cylinder;

a hand knob connected to the free end of said piston rod extending outside of said cylinder;

an outlet, provided with an outlet check valve, connected to said cylinder at the end remote from said piston rod;

an inlet, provided with an inlet check valve, connected to said cylinder at the end remote from said piston rod; and a connector, communicating with said inlet, connectable to said connecting hose.

3. A device in accordance with claim 2 wherein said hand knob further includes a detent projection thereon and wherein said suction means further includes a lock hook engageable with said detent projection when said piston rod is fully depressed, a spring retaining said lock hook in the engaged position, and an operating button connected to said lock hook to cause a release thereof from the engaged position, against the force of said spring, when said button is depressed.

4. A device in accordance with claim 3 wherein said cylindrical container is made of plastic and wherein said suction means is disposed remote from said cylindrical container.

5. A device in accordance with claim 2 wherein said suction means comprises an arrangement of two or more of said cylinders in a common block, each said cylinder being provided with a corresponding one of said suction means piston, said piton rod, said hand knob, said outlet and said inlet, and further including a manifold connecting the inlets of several or all of said cylinders of said block.

6. A device in accordance with claim 5, wherein said suction means further includes a further inlet check valve between said manifold and said connector, said further check valve additionally preventing the flowing out of air from the manifold into said connecting hose.

7. A device in accordance with claim 1 wherein said piston in said cylindrical receiving container possesses no piston rod.

8. A device in accordance with claim 7 wherein the opening in said one end of said container is arranged concentrically to the axis of said cylindrical container.

9. A device in accordance with claim 1 wherein said connecting hose includes a connecting nipple which is air-tightly insertable into the opening in said cylindrical container.

10. A device in accordance with claim 9 wherein the end of said connecting nipple projecting into said cylindrical container possesses a tapered peripheral surface and wherein said piston, at the bottom side thereof facing the opening in said one end of said container, centrally possesses a tapered blind hole complementary to the taper of said connecting nipple.

11. A device in accordance with claim 10 wherein said container further includes an annular shoulder projecting from the internal wall thereof, in the vicinity of said one end having said opening, for supporting said piston.

12. A device in accordance with claim 11 wherein the dimensioning and relative association of said piston, said connecting nipple, and said shoulder are effected in such a way that upon abutment of the retracted piston with the connecting nipple and upon sealing thereof by the tapered blind hole in said piston there is a slight spacing between the bottom end of said piston and said shoulder.

13. A device in accordance with claim 12 wherein said tapered blind hole in said piston comprises a concentrically arranged boss, having an inwardly tapered peripheral surface, projecting from the side of said piston facing the opening in said one end of said container, the tapered blind hole extending from the free end of the boss thereinto, and wherein said container further includes a collar having a tapered internal surface projecting upwardly from said one end of said cylindrical container around said opening, the external taper of said boss, upon abutment of said piston with said shoulder, sealingly engaging in the tapered bore of said collar.

14. A device in accordance with claim 1 wherein the bore of said connecting socket opening into said cylindrical container is closed by a tearable film.

15. A device in accordance with claim 1, wherein said connecting socket comprises:

a cap, screw-threadedly connected to the end of said cylindrical container, said cap having a bore in the end face thereof; and a plug of a soft resilient material inserted into the bore of said cap and having a weakened portion sealing the interior of said cylindrical container.

16. A device in accordance with claim 15 further including a cannula connected to said connecting socket, said cannula being pointed at both ends and having a grip member intermediate said ends.

* * * * *